United States Patent [19]

Hogue et al.

[11] 3,989,637

[45] Nov. 2, 1976

[54] CORROSION INHIBITORS AND PROCESSES FOR USING THE SAME

[75] Inventors: Ronald D. Hogue, Manchester; Thomas M. King, Creve Coeur; Robert S. Mitchell, Webster Groves, all of Mo.

[73] Assignee: Monsanto Company, St. Louis, Mo.

[22] Filed: June 2, 1975

[21] Appl. No.: 583,073

[52] U.S. Cl. .............................. 252/180; 21/2.7 R; 210/58; 252/388
[51] Int. Cl.² ...................... C02B 1/00; C02B 3/06
[58] Field of Search ............... 260/340.2; 252/180, 252/389, 388; 21/2.7 R; 210/58

[56] References Cited
UNITED STATES PATENTS

| | | | |
|---|---|---|---|
| 699,422 | 5/1902 | Sternberg | 260/340.2 |
| 3,173,925 | 3/1965 | Seeliger | 260/340.2 |
| 3,295,917 | 1/1967 | Cotton et al. | 252/389 R |
| 3,763,189 | 10/1973 | Harken | 260/340.2 |

*Primary Examiner*—Mayer Weinblatt
*Assistant Examiner*—Edith R. Buffalow
*Attorney, Agent, or Firm*—Thomas B. Leslie

[57] ABSTRACT

Carboxylated lactones of the general formula

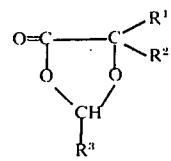

wherein $R^1$ and $R^2$ are individually selected from hydrogen, hydroxy, alkyl, hydroxyalkyl, —COOM, —CHOHCOOM, —CH₂COOM and a 1,3-dioxolane, 5-oxo group, and $R^3$ is selected from hydrogen and —COOM, wherein M is hydrogen, alkali metal, ammonium or alkylammonium, provided that at least one of $R^1$, $R^2$ and $R^3$ contain a carboxyl group, are disclosed as inhibiting the corrosion of metals by oxygen-bearing waters. The carboxylated lactones can be employed either alone or in combination with thiols, 1,2,3-triazoles, zinc salts, chromates, silicates, inorganic phosphates, molybdates, tannins, lignins, lignin sulfonates, calcium and magnesium salts and mixtures thereof.

20 Claims, No Drawings

CORROSION INHIBITORS AND PROCESSES FOR USING THE SAME

BACKGROUND OF THE INVENTION

The present invention relates to corrosion inhibiting compositions and to methods of inhibiting corrosion of metal surfaces in contact with an aqueous medium of corrosive nature. More particularly, this invention relates to methods of inhibiting the corrosion of metal surfaces by utilizing in the corrosive aqueous medium certain carboxylated lactones which do not require the addition of heavy metal ions to effectively inhibit corrosion.

The present invention has special utility in the prevention of the corrosion of metals which are in contact with circulating water, that is water which is moving through condensers, heat exchanges, cooling towers, evaporators or distribution systems; however, it can be used to prevent the corrosion of metal surfaces in other aqueous corrosive media. This invention is especially valuable in inhibiting the corrosion of ferrous metals including iron and steel, and also galvanized steel, and nonferrous metals including copper and its alloys, aluminum and its alloys and brass. These metals are generally used in circulating water systems.

The major corrosive ingredients of aqueous cooling systems are primarily dissolved oxygen and inorganic salts, such as the carbonate, bicarbonate, chloride and/or sulfate salts of calcium, magnesium and/or sodium. Other factors contributing to corrosion are pH and temperature. Generally an increase in the temperature and a decrease in the pH accelerates corrosion.

It is well known that certain corrosion inhibiting compositions are enhanced in their effectiveness by the addition of water soluble zinc salts and/or chromates to the inhibiting compositions. However, the use of zinc salts and chromates have been found in recent years to adversely affect water quality when released into waste treatment systems or natural waters, and also to affect the surrounding environment when released in cooling tower drift. Removal or recycle of the zinc and/or chromate ions by precipitation or other treatments is complicated and expensive. Consequently, effective corrosion inhibiting compositions free of such heavy metal ions are now desired by industry for protection of metallic equipment without the accompanying disadvantages of the heavy metal ions previously employed.

SUMMARY OF THE INVENTION

It is a primary object of this invention to provide new corrosion inhibiting methods for metals.

It is another object of this invention to provide new corrosion inhibiting methods for ferrous metals including iron and steel and nonferrous metals including copper and brass.

It is another object of this invention to provide new corrosion inhibiting methods for ferrous metals and nonferrous metals in contact with an aqueous corrosive medium.

It is another object of this invention to provide new corrosion inhibiting methods for ferrous metals and nonferrous metals in contact with cooling waters.

Other advantages and objects of the present invention will be apparent from the following discussion.

It has been found that certain carboxylated lactones unexpectedly function as excellent corrosion inhibitors and do not require the presence of heavy metal ions to be effective, although they can be used in conjunction with all well-known water treating ingredients without being adversely affected in their corrosion inhibiting properties. The nature of these carboxylated lactones and methods of use thereof as corrosion inhibitors are more fully set forth in the description of preferred embodiments below.

DESCRIPTION OF PREFERRED EMBODIMENTS

The carboxylated lactones useful in the present invention have the following formula:

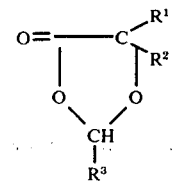

wherein $R^1$ and $R^2$ are individually selected from hydrogen, hydroxy, alkyl, hydroxyalkyl, —COOM, —CHOHCOOM, —CH$_2$COOM and a 1,3-dioxolane, 5-oxo group, and $R^3$ is selected from hydrogen and —COOM, wherein M is hydrogen, alkali metal, ammonium or alkylammonium, provided that at least one of $R^1$, $R^2$ and $R^3$ contains a carboxyl group.

In the above formulae M can be alike or unlike and is selected from the group of alkali metal ions, ammonium, or alkylammonium and hydrogen or any cation which will yield sufficient solubility in the aqueous corrosive media to function as a corrosion inhibitor. In particular, those alkylammonium ions derived from amines having a low molecular weight, such as below about 300, and more particularly the alkyl amines, alkylene amines, and alkanol amines containing not more than two amine groups, such as ethylamine, diethylamine, propylamine, propylene diamine, hexylamine, 2-ethylhexylamine, N-butyl ethanol amine, triethanol amine and the like are the preferred amines. It is to be understood that the preferred metal ions are those which render the compound a water-soluble salt in concentrations of at least 10 and preferably 100 parts per million in aqueous solution, such as the alkali metals, as well as the water-soluble salts from ammonium, alkyl ammonium and alkanol amine ions.

Illustrative but without limitation, of the carboxylated lactone corrosion inhibitors of the present invention are those shown below:

| Compound No. | Compound | Formula |
|---|---|---|
| 1 | 1,3-dioxolane-4,4-diacetic acid, 5-oxo | 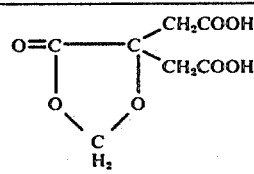 |
| 2 | 1,3-dioxolane-2-carboxy-4,4-diacetic acid, 5-oxo | 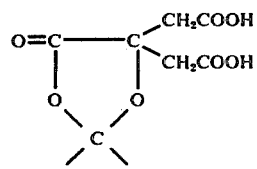 |
| 3 | 1,3-dioxolane-4-acetic acid, 5-oxo | 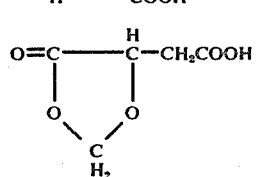 |
| 4 | 1,3-dioxolane-2-carboxy-4-methyl, 5-oxo | 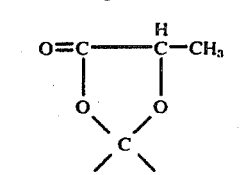 |
| 5 | 1,3-dioxolane-2-carboxy, 5-oxo | 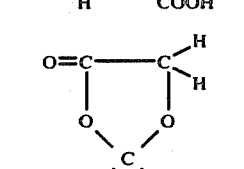 |
| 6 | 1,3-dioxolane-4-hydroxy acetic acid, 5-oxo | 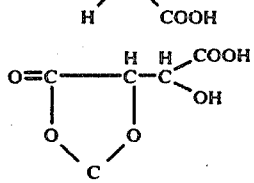 |
| 7 | 2,2'-dicarboxy-4,4'-bis(1,3-dioxolane, 5-oxo) | 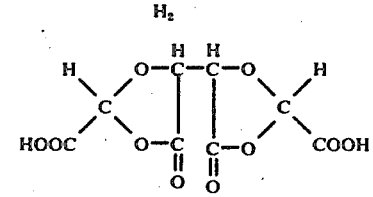 |
| 8 | 2,2'-dicarboxy-4,4'-bis(1,3-dioxolane-4-hydroxy, 5-oxo) | 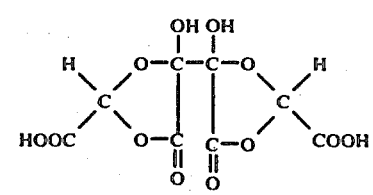 |

The carboxylated lactones of the present invention are prepared by known methods, in general. In the case of those lactones derived from the polycarboxylic oxyacids such as citric, malic and tartaric acids condensed with formaldehyde the reaction can be carried out by the methods set out by C. A. L. de Bruyn and W. A. van Ekenstein in Recuil des Travaux Chemiques Pay-Bas et de la Belgique, 20, pp. 331–343 (1901). In that paper the authors demonstrate that the carboxylated oxyacids react with trioxymethylene in solvents such as chloroform at elevated temperatures of from about 90° to 160° C. with evaporation of the excess formaldehyde and water or upon distillation of water with benzene and crystallization from benzene solvent. The poly- and monocarboxylic oxyacids can also be reacted with oxyethanoic, i.e., glyoxalic, acid or glyoxylic acid which serves as the source of a carboxylic substituent upon the dioxolane ring formed by the condensation reaction. The reactions are preferably carried out in the presence of an acid catalyst such as hydrochloric acid, sulfuric acid, benzene sulfonic acid, p-toluene sulfonic acid, dichloroacetic acid, trichloroacetic acid, oxalic acid or the like. The carboxylic acid substituted lactone products can be recrystallized from water, and common organic solvents such as ethyl ether, ethanol, methanol, chloroform, benzene or toluene. The alkali metal, ammonium and alkylammonium salts of the carboxylated lactones are produced by partial or full neutralization of the carboxy groups with the corresponding hydroxide, carbonate or the like.

The carboxylated lactone corrosion inhibitors of the present invention effectively inhibit corrosion when utilized at at least three parts per million, preferably from about 10 ppm to about 500 ppm, and more preferably from about 10 ppm to 150 ppm in the corrosive medium. It is to be understood that greater than 500 ppm of these carboxylated lactones can be utilized if desired so long as the higher amounts are not detrimental to the water system. Amounts as low as 1 ppm are effective under some conditions.

The carboxylated lactone corrosion inhibitors of the present invention are effective in both acidic or basic aqueous corrosive media. The pH can range from about 4 to about 12. For example, Compound No. 1 set forth above when used in amounts of from about 3 ppm to 150 ppm is an effective corrosion inhibitor in an aqueous corrosive medium where the pH is from about 4 to about 12. In cooling towers, the water system is generally maintained at a pH of from about 6.5 to 10.0, and most often at a pH of from about 6.5 to 8.5. In all such systems the inhibitors of the present invention are effective.

When the water systems are in contact with various metals such as steel and copper or copper-containing metals, it is frequently desirable to use, along with the carboxylated lactone corrosion inhibitors a 1,2,3-triazole such as 1,2,3-benzotriazole or 1,2,3-tolyltriazole or a thiol of a thiazole, an oxazole or an imidazole such as are known in the art to inhibit the corrosion of copper. These azoles are likewise effective with the carboxylated lactones of the present invention. The amounts of the azoles used depend on the particular aqueous system. Generally concentrations of about 0.05 to 5 ppm thiol or triazole with about 3 to 150 ppm of carboxylated lactones of this invention are satisfactory.

It is within the scope of the present invention that the carboxylated lactone corrosion inhibitors may also be used in aqueous systems which contain various inorganic and/or organic materials, particularly all ingredients or substances used by the water-treating industry, with the proviso that such materials do not render the lactones substantially ineffective for the desired purpose of corrosion inhibition. In some instances, there can be a cooperative effect between the lactones of this invention and the other added materials. For example, the carboxylated lactones of the present invention can be employed with both zinc salts and/or chromates in the inhibition of corrosion in an aqueous corrosive medium.

Others of these organic and inorganic materials which can be used effectively with the carboxylated lactones of the present invention include, without limitation, polycarboxylates, particularly those whose molecular weights are from about 2,000 to about 20,000 and from about 20,000 to 960,000; antifoam agents; water soluble polymers such as polyacrylic and polymethacrylic acid, polyacrylamide, partially hydrolyzed acrylamide and the like; tannins; lignins; deaerating materials; polymeric anhydrides (such as polymaleic anhydride); and sulfonated lignins. Other materials which can be used with said inhibitors include, for example, surface active agents, acetodiphosphonic acids, inorganic phosphates including orthophosphates, molecularly dehydrated phosphates, phosphonates, polyfunctional phosphated polyol esters, molybdates nitrites, calcium and magnesium salts such as calcium or magnesium chlorides, sulfates, nitrates and bicarbonates and inorganic silicates. Furthermore, scale and precipitation inhibitors such as amino tri(methylene phosphonic acid) may be used in combination with the inhibitors of the present invention. For exemplary purposes only, these other precipitation inhibitors are described in U.S. Pat. Nos. 3,234,124; 3,336,221; 3,393,150; 3,214,454; 3,400,148; 3,434,969; 3,451,939; 3,462,365; 3,480,083; 3,591,513; 3,597,352 and 3,644,205, all of which publications are incorporated herein by reference. Other corrosion inhibitors can be used in combination with the carboxylated lactones including those described in U.S. Pat. Nos. 3,483,133; 3,487,018; 3,518,203; 3,532,639; 3,580,855; and 3,816,333; all of which are incorporated herein by reference.

The following examples are included to illustrate the practice of the present invention and the advantages provided thereby but are not to be considered limiting. Unless otherwise specified, all parts are parts by weight and all temperatures are in degrees centigrade.

EXAMPLE A 1,3-Dioxolane-4,4-diacetic acid, 5-oxy (Compound 1) is prepared in the following manner. There is charged to a reaction flask 2.5 liters of benzene and .5 liter of dioxane and then there is dissolved therein 2 parts p-toluene sulfonic acid, 420 parts of citric acid monohydrate and 60 parts of trioxymethylene. The mixture is refluxed for 48 hours while separating water formed. 15 Parts of trioxymethylene are then added and refluxing continued for 6 hours. The reaction mixture is cooled to 50° C. to 60° C., the supernatant organic layer decanted and the solids remaining recrystallized from water. Additional cooling yields an additional crop of crystals identified as the desired 1,3-dioxolane-4,4-diacetic acid, 5-oxo. Titration of a sample of the dicarboxyl lactone in water with sodium hydroxide solution to neutral pH produces the monosodium salt of the lactone and to a pH of 9.5 produces the disodium salt thereof.

In the same manner as described above, Compounds 3 and 6 are produced from malic and tartaric acids respectively. In like manner Compounds 2, 4, 5, 7 and 8 are produced by reaction of citric, lactic, glycolic, tartaric and dihydroxy tartaric acids with glyoxylic acid, in the last instances in a 1:2 mol ratio. The carboxylic acid substituted lactones are neutralized in the same way from water solution to produce the monosodium or monoammonium salts of Compounds 3, 4, 5 and 6, the disodium or diammonium salts of Compounds 7 and 8 and the di and tri salts of Compound 2.

The effectiveness of the carboxylated lactones of this invention as inhibitors of the corrosion of metals by oxygenated waters is shown by tests determining metallic corrosion rates. The tests are conducted in polarization test cells employing steel electrodes with synthetic, very hard municipal water adjusted to an initial pH of 7.0 and with continuous aeration. The concentrations of the inhibitors are calculated on the basis of active acid form of the carboxylated lactone. The corrosion tests are generally carried out at two concentrations of 50 and 150 ppm of the synthetic hard water test medium. The rates of corrosion are determined by the Tafel Slope Extrapolation Method as described in "Handbook of Corrosion, Testing and Evaluation" by Dean, France and Ketchum published by Wiley-Interscience, New York (1971), Chapter 8, from the observed current densities and electrode potentials and are expressed in terms of mils per year of metal loss. The corrosion rates of the steel electrodes, when protected by the test concentrations of the corrosion inhibitors tested, can then be compared to the corrosion rate of those electrodes when unprotected by a corrosion inhibitor. The decrease in the corrosion rate expressed in mils per year indicates the effectiveness of the corrosion inhibitor.

In tests of this nature, where the aqueous corrosion medium is synthetic hard municipal water at only slightly elevated temperature, any corrosion rate less than the corrosion rate of the medium alone is desired and rates of less than about 10 mils per year are highly desired and substances that give this rate or lower are considered excellent. This does not mean, however, that substances having a corrosion rate of more than 10 m.p.y. are not valuable; depending upon the particular conditions a compound or composition having a higher corrosion rate may be used, as an instance where the equipment will be used only for a short period of time.

The synthetic hard municipal water used in the test described is prepared to approximate very hard municipal water as follows:

| INGREDIENTS | MG/L |
| --- | --- |
| Calcium | 88 |
| Magnesium | 24 |
| Chloride | 70 |
| Sulfate | 328 |
| Bicarbonate | 40 |
| Total hardness, as CaCO$_3$ in distilled water | 319 |

Tests determining the metallic corrosion rates in oxygenated water established by the carboxylated lactones of this invention are set out in the following examples:

EXAMPLE I

The corrosion rates of a steel electrode at 35° C. in the synthetic hard municipal water medium described above without added inhibitor and containing the indicated concentration of Compound No. 1, 1,3-dioxolane-4,4-diacetic acid, 5-oxo, and Compound No. 2, 1,3-dioxolane-2-carboxy-4,4-diacetic acid, 5-oxo, are determined as above by the Tafel Slope Extrapolation Method. The results are set out in TABLE I below:

TABLE I

| Test Compound | Concentration of Corrosion Inhibitor (ppm) | Corrosion Rate (m.p.y.) | % Reduction |
| --- | --- | --- | --- |
| Control | None | 42 | — |
| 1 | 50 | 12 | 71 |
|   | 150 | 3 | 93 |
| 2 | 50 | 16 | 62 |
|   | 150 | 2 | 95 |

EXAMPLE II

Additional tests are conducted in the same manner as in EXAMPLE I above with Compounds 3 through 8 at the same two concentrations of active carboxylated lactone inhibitor. The results utilizing these corrosion inhibiting compounds are similar to those obtained in EXAMPLE I in that the rates of corrosion reduction range from about 50 to about 95 percent in mils per year in the same corrosive aerated synthetic water medium.

The foregoing examples have been described in the specification for the purpose of illustration and not limitation. The corrosion inhibiting compounds of this invention can be employed in a number of forms which will give good protection against corrosion. For example, the carboxylated lactones, either in the form of acids or salts, alone or in combination with other corrosion and scale inhibiting materials, as outlined above, including thiols, 1,2,3-triazoles, and the nitrites, zinc salts, chromates, silicates, inorganic phosphates, molybdates, tannins, lignins, lignin sulfonates, and calcium and/or magnesium salts, can simply be dissolved by mixing them into the aqueous corrosive medium. In another method they can be dissolved separately in water or another suitable solvent and then intermixed with the aqueous corrosive medium.

Various means are available to insure that the correct proportion of corrosion inhibitor is present in the corrosive medium. For example, a solution containing the said corrosion inhibitor can be metered into the corrosive medium by drop feeder. Another method is to formulate tablets or briquettes of a solid carboxylated lactone, with or without other ingredients, and these can be added to the corrosive medium. The said solid, after briquetting, can be used in a standard ball feeder so that the solid is released slowly in the corrosive medium.

We do not intend to be limited to any compounds, compositions or methods disclosed herein for illustrative purposes. Our invention may be otherwise practiced and embodied within the scope of the following claims.

What is claimed is:

1. A method of inhibiting the corrosion of metals in contact with an aqueous corrosive medium which comprises maintaining in said medium a carboxylated lactone having the formula

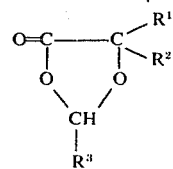

wherein $R^1$ and $R^2$ are individually selected from the group consisting of hydrogen, hydroxy, alkyl, hydroxyalkyl, —COOM, —CHOHCOOM, —CH$_2$COOM and a 1,3-dioxolane, 5-oxo group, and $R^3$ is selected from hydrogen and —COOM, wherein M is selected from the group consisting of hydrogen, alkali metal, ammonium and alkylammonium, provided that at least one of $R^1$, $R^2$ and $R^3$ contains a carboxyl group.

2. The method of claim 1 wherein the amount of said carboxylated lactone maintained in said medium is from about 3 to about 500 parts per million.

3. The method of claim 1 wherein the amount of said carboxylated lactone maintained in said medium is at least about 3 parts per million.

4. The method of claim 1 wherein the said inhibited metals are selected from the group consisting of ferrous metals, copper, aluminum and brass.

5. The method of claim 1 wherein each M is hydrogen.

6. The method of claim 1 wherein at least one M is an alkali metal ion.

7. The method of claim 1 wherein at least one M is an ammonium ion.

8. The method of claim 6 wherein at least one M is hydrogen.

9. The method of claim 1 wherein at least one of $R^1$ and $R^2$ is —CH$_2$COOM.

10. The method of claim 1 wherein $R^3$ is —COOM.

11. The method of claim 1 wherein $R^1$ or $R^2$ is, 1,3-dioxolane, 5-oxo group.

12. The method of claim 1 wherein at least one inhibited metal is copper and the aqueous medium additionally contains a compound selected from the group consisting of 1,2,3-triazoles, thiols of thiazoles, thiols of oxazoles, thiols of imidazoles and mixtures thereof in an amount of at least 0.05 parts per million.

13. The method of claim 1 wherein the lactone is the acid or salt of 1,3-dioxolane-4-acetic acid, 5-oxo.

14. The method of claim 1 wherein the lactone is the acid or salt of 1,3-dioxolane-2-carboxy-4-methyl, 5-oxo.

15. The method of claim 1 wherein the lactone is the acid or salt of 1,3-dioxolane-2-carboxy, 5-oxo.

16. The method of claim 1 wherein the lactone is the acid or salt of 1,3-dioxolane-4-hydroxy acetic acid, 5-oxo.

17. The method of claim 1 wherein the lactone is the acid or salt of 2,2'-dicarboxy-4,4'-bis(1,3-dioxolane, 5-oxo).

18. The method of claim 1 wherein the lactone is the acid or salt of 2,2'-dicarboxy-4,4'-bis(1,3-dioxolane-4-hydroxy, 5-oxo).

19. The method of inhibiting the corrosion of metals in contact with an aqueous corrosive medium which comprises maintaining in said medium at least about 3 parts per million of the acid or alkali metal, ammonium or alkylammonium salt of 1,3-dioxolane-4,4-diacetic acid, 5-oxo.

20. The method of inhibiting the corrosion of metals in contact with an aqueous corrosive medium which comprises maintaining in said medium at least about 3 parts per million of the acid or alkali metal, ammonium or alkylammonium salt of 1,3-dioxolane-2-carboxy-4,4-diacetic acid, 5-oxo.

* * * * *